United States Patent
Wang et al.

(10) Patent No.: US 9,993,613 B2
(45) Date of Patent: Jun. 12, 2018

(54) GUIDE EXTENSION CATHETER

(71) Applicant: BOSTON SCIENTIFIC SCIMED, INC., Maple Grove, MN (US)

(72) Inventors: Huisun Wang, Maple Grove, MN (US); Joel M. Wasdyke, Eden Prairie, MN (US); Wayne Falk, Minneapolis, MN (US); Brian R. Reynolds, Ramsey, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1008 days.

(21) Appl. No.: 13/671,317

(22) Filed: Nov. 7, 2012

(65) Prior Publication Data

US 2013/0116701 A1    May 9, 2013

Related U.S. Application Data

(60) Provisional application No. 61/557,766, filed on Nov. 9, 2011.

(51) Int. Cl.
*A61M 25/01*    (2006.01)
*A61M 25/00*    (2006.01)

(52) U.S. Cl.
CPC ........ *A61M 25/01* (2013.01); *A61M 25/0069* (2013.01); *A61M 25/0102* (2013.01); *A61M 2025/0004* (2013.01)

(58) Field of Classification Search
CPC ...... A61M 2025/0004; A61M 25/0069; A61M 25/0102; A61M 25/01; A61M 2025/0681; A61B 2018/00386

USPC .......... 606/108; 604/164.13, 170.01, 170.02, 604/264, 523, 524, 528
See application file for complete search history.

(56) References Cited

U.S. PATENT DOCUMENTS

| | | | |
|---|---|---|---|
| 4,564,014 A | 1/1986 | Fogarty et al. |
| 4,616,652 A | 10/1986 | Simpson et al. |
| 4,762,129 A | 8/1988 | Bonzel et al. |
| 5,106,455 A | 4/1992 | Jacobsen et al. |
| 5,120,323 A | 6/1992 | Shockey et al. |
| 5,232,445 A | 8/1993 | Bonzel et al. |
| 5,238,004 A | 8/1993 | Sahatjian et al. |
| 5,267,982 A | 12/1993 | Sylvanowicz |

(Continued)

FOREIGN PATENT DOCUMENTS

| | | |
|---|---|---|
| DE | 3819372 C1 | 1/1990 |
| EP | 0277366 A1 | 8/1988 |

(Continued)

*Primary Examiner* — Ryan J Severson
*Assistant Examiner* — Charles Wei
(74) *Attorney, Agent, or Firm* — Seager, Tufte & Wickhem, LLP (57) ABSTRACT

Medical devices and methods for making and using medical devices are disclosed. An example medical device may include a guide extension catheter. The guide extension catheter may include a proximal tubular member having a lumen defined therein. A distal tubular member may be attached to the proximal tubular member. The proximal tubular member may have an outer diameter. The distal tubular member may have an inner diameter. The inner diameter of the distal tubular member may be greater than the outer diameter of the proximal tubular member. A stiffening member may be slidably disposed within the proximal tubular member.

17 Claims, 10 Drawing Sheets

(56) References Cited

U.S. PATENT DOCUMENTS

| | | | |
|---|---|---|---|
| 5,385,562 A | 1/1995 | Adams et al. | |
| 5,415,639 A | 5/1995 | VandenEinde et al. | |
| 5,441,489 A | 8/1995 | Utsumi et al. | |
| 5,484,407 A * | 1/1996 | Osypka | 604/95.04 |
| 5,527,292 A * | 6/1996 | Adams et al. | 604/171 |
| 5,636,634 A * | 6/1997 | Kordis | A61B 5/0422 600/374 |
| 5,662,606 A * | 9/1997 | Cimino et al. | 604/95.04 |
| 5,772,609 A | 6/1998 | Nguyen et al. | |
| 5,928,191 A | 7/1999 | Houser et al. | |
| 6,066,126 A | 5/2000 | Li et al. | |
| 6,139,510 A | 10/2000 | Palermo | |
| 6,159,195 A * | 12/2000 | Ha et al. | 604/500 |
| 6,508,803 B1 | 1/2003 | Horikawa et al. | |
| 6,544,215 B1 * | 4/2003 | Bencini et al. | 604/95.01 |
| 6,575,958 B1 | 6/2003 | Happ et al. | |
| 6,579,246 B2 | 6/2003 | Jacobsen et al. | |
| 6,623,268 B2 | 9/2003 | Diamond et al. | |
| 6,638,268 B2 | 10/2003 | Niazi | |
| 6,695,793 B2 | 2/2004 | Brennan et al. | |
| 6,766,720 B1 | 7/2004 | Jacobsen et al. | |
| 6,866,655 B2 | 3/2005 | Hackett | |
| 6,953,454 B2 | 10/2005 | Peterson et al. | |
| 6,979,319 B2 | 12/2005 | Manning et al. | |
| 7,241,273 B2 | 7/2007 | Maguire | |
| 7,294,121 B2 | 11/2007 | Kawata et al. | |
| 7,294,124 B2 | 11/2007 | Eidenschink | |
| 7,316,678 B2 | 1/2008 | Nash et al. | |
| 7,604,612 B2 | 10/2009 | Ressemann et al. | |
| 7,717,899 B2 | 5/2010 | Bowe et al. | |
| 7,736,355 B2 | 6/2010 | Itou et al. | |
| 7,762,984 B2 | 7/2010 | Kumoyama et al. | |
| 8,048,032 B2 | 11/2011 | Root et al. | |
| 8,142,412 B2 | 3/2012 | Hehrlein et al. | |
| 8,142,413 B2 | 3/2012 | Root et al. | |
| 8,292,850 B2 | 10/2012 | Root et al. | |
| 8,298,178 B2 | 10/2012 | Carrillo et al. | |
| 8,465,456 B2 | 6/2013 | Stivland | |
| 2003/0050600 A1 * | 3/2003 | Ressemann et al. | 604/101.01 |
| 2003/0069522 A1 | 4/2003 | Jacobsen et al. | |
| 2004/0059179 A1 | 3/2004 | Maguire et al. | |
| 2004/0116832 A1 | 6/2004 | Friedrich et al. | |
| 2004/0116848 A1 * | 6/2004 | Gardeski | A61M 25/0147 604/95.01 |
| 2004/0181174 A2 | 9/2004 | Davis et al. | |
| 2005/0070844 A1 | 3/2005 | Chow et al. | |
| 2005/0080430 A1 | 4/2005 | Wright et al. | |
| 2005/0107817 A1 | 5/2005 | White et al. | |
| 2005/0267442 A1 | 12/2005 | Von Oepen | |
| 2006/0063973 A1 * | 3/2006 | Makower | A61B 1/00135 600/114 |
| 2007/0260219 A1 * | 11/2007 | Root et al. | 604/523 |
| 2008/0051760 A1 * | 2/2008 | Schoenle et al. | 604/523 |
| 2008/0167628 A1 | 7/2008 | Li et al. | |
| 2008/0181174 A1 | 7/2008 | Cho | |
| 2009/0177120 A1 | 7/2009 | Tockman et al. | |
| 2009/0264865 A1 * | 10/2009 | Kawai | 604/528 |
| 2010/0030186 A1 | 2/2010 | Stivland | |
| 2010/0198160 A1 | 8/2010 | Voss | |
| 2010/0211050 A1 | 8/2010 | Luther | |
| 2010/0234876 A1 | 9/2010 | Watson | |
| 2011/0172520 A1 | 7/2011 | Lentz | |
| 2011/0301502 A1 | 12/2011 | Gill | |
| 2012/0234876 A1 | 9/2012 | Diamond et al. | |
| 2015/0165175 A1 * | 6/2015 | Evard | A61M 25/10 606/196 |

FOREIGN PATENT DOCUMENTS

| | | |
|---|---|---|
| EP | 0564894 A1 | 10/1993 |
| EP | 0710490 A3 | 12/1996 |
| EP | 1656963 B1 | 11/2007 |
| EP | 1639951 B1 | 4/2009 |
| EP | 2138200 B1 | 2/2013 |
| WO | 0141858 A3 | 1/2002 |
| WO | 03049798 A8 | 5/2004 |
| WO | 2005018728 A3 | 6/2005 |
| WO | 2006045809 A1 | 5/2006 |
| WO | 2006119422 A3 | 9/2007 |

* cited by examiner

GUIDE EXTENSION CATHETER

CROSS-REFERENCE TO RELATED APPLICATIONS

This application claims priority under 35 U.S.C. § 119 to U.S. Provisional Application Ser. No. 61/557,766, filed Nov. 9, 2011, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a guide extension catheter.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a guide extension catheter. The guide extension catheter may include a proximal tubular member having a lumen defined therein. A distal tubular member may be attached to the proximal tubular member. The proximal tubular member may have an outer diameter. The distal tubular member may have an inner diameter. The inner diameter of the distal tubular member may be greater than the outer diameter of the proximal tubular member. A stiffening member may be slidably disposed within the proximal tubular member.

Also disclosed are catheter systems for improving access to a coronary artery. An example catheter system may include a guide catheter having a distal end. A guide extension catheter may be disposed within the guide catheter. The guide extension catheter may include a proximal tubular member having a lumen defined therein, a distal tubular member attached to the proximal tubular member, and a stiffening member slidably disposed within the proximal tubular member. A distal end of the guide extension catheter may be configured to extend distally beyond the distal end of the guide catheter and into a coronary artery. A treatment catheter may be disposed within the guide catheter.

Methods for accessing a coronary artery are also disclosed. An example method may include providing a guide catheter, advancing the guide catheter through a blood vessel to a position adjacent to an ostium of a coronary artery, and providing a guide extension catheter. The guide extension catheter may include a proximal tubular member having a lumen defined therein, a distal tubular member attached to the proximal tubular member, and a stiffening member slidably disposed within the proximal tubular member. The method may also include advancing the guide extension catheter through the guide catheter to a position where at least a portion of the distal tubular member extends distally beyond a distal end of the guide catheter and into the coronary artery and advancing a treatment catheter through the guide catheter.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Figure 1:
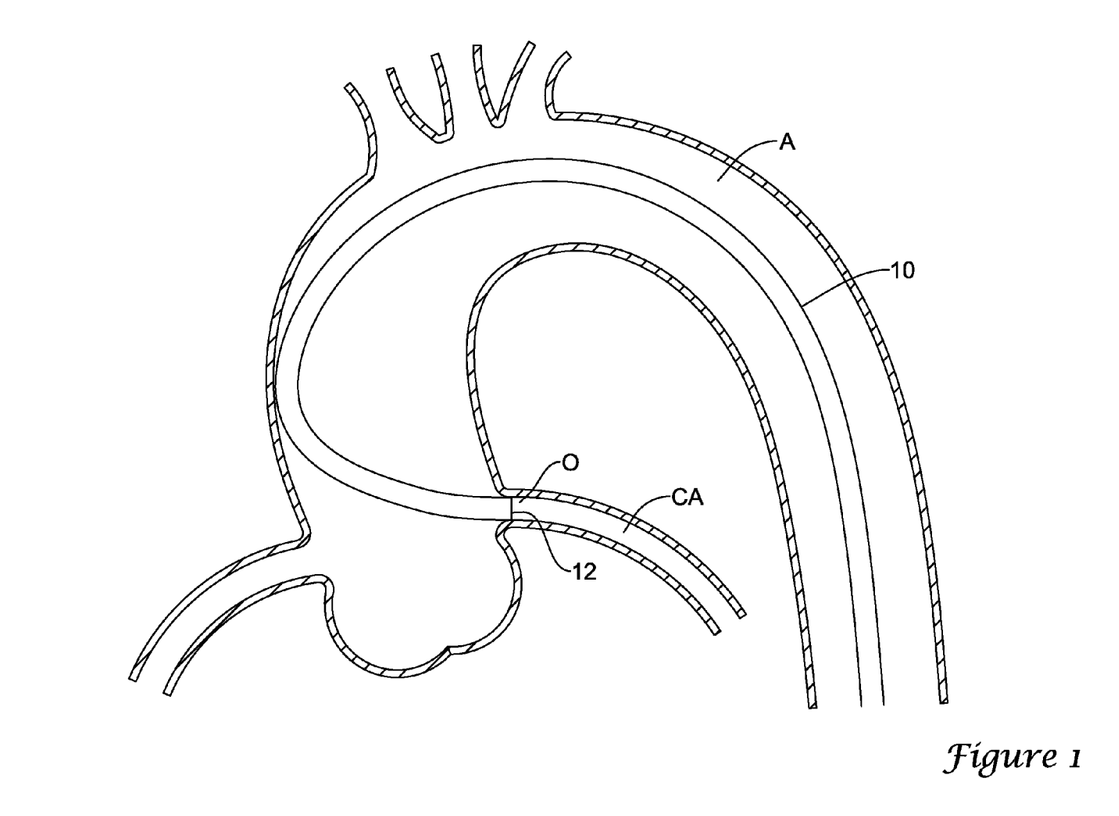
FIG. 1 is a plan view illustrating an example guide catheter advanced through the aorta to the ostium of a coronary artery.

Minimally-invasive cardiac interventions such as percutaneous transluminal coronary angioplasty are widely utilized throughout the world. These procedures may include the use of a guide catheter. For example, a guide catheter 10 may be advanced through a blood vessel such as the aorta A to a position adjacent to the ostium O of a (e.g., left and/or right) coronary artery CA as illustrated in FIG. 1. When so positioned, a treatment catheter (e.g., balloon catheter, stent delivery system, etc.) may be advanced through guide catheter 10 and into the coronary artery CA to a target location where the treatment catheter may be used to perform the appropriate cardiac intervention.

In order for the treatment catheter to efficiently reach the intended target location, maintaining the position of guide catheter 10 at the ostium O of the coronary artery CA may be desirable. For example, given that the heart may be beating during the intervention (and/or other factors), the guide catheter 10 may lose its positioning or otherwise be shifted so that it no longer is positioned to efficiently guide the treatment catheter to the coronary arteries. This may include a distal end 12 of guide catheter 10 being shifted away from the ostium O of the coronary artery CA. Because of the shift away from the ostium O, access to the coronary arteries CA may require repositioning of guide catheter 10 in order to bring the distal end 12 back into engagement with the ostium O of the coronary artery CA.

Figure 2:
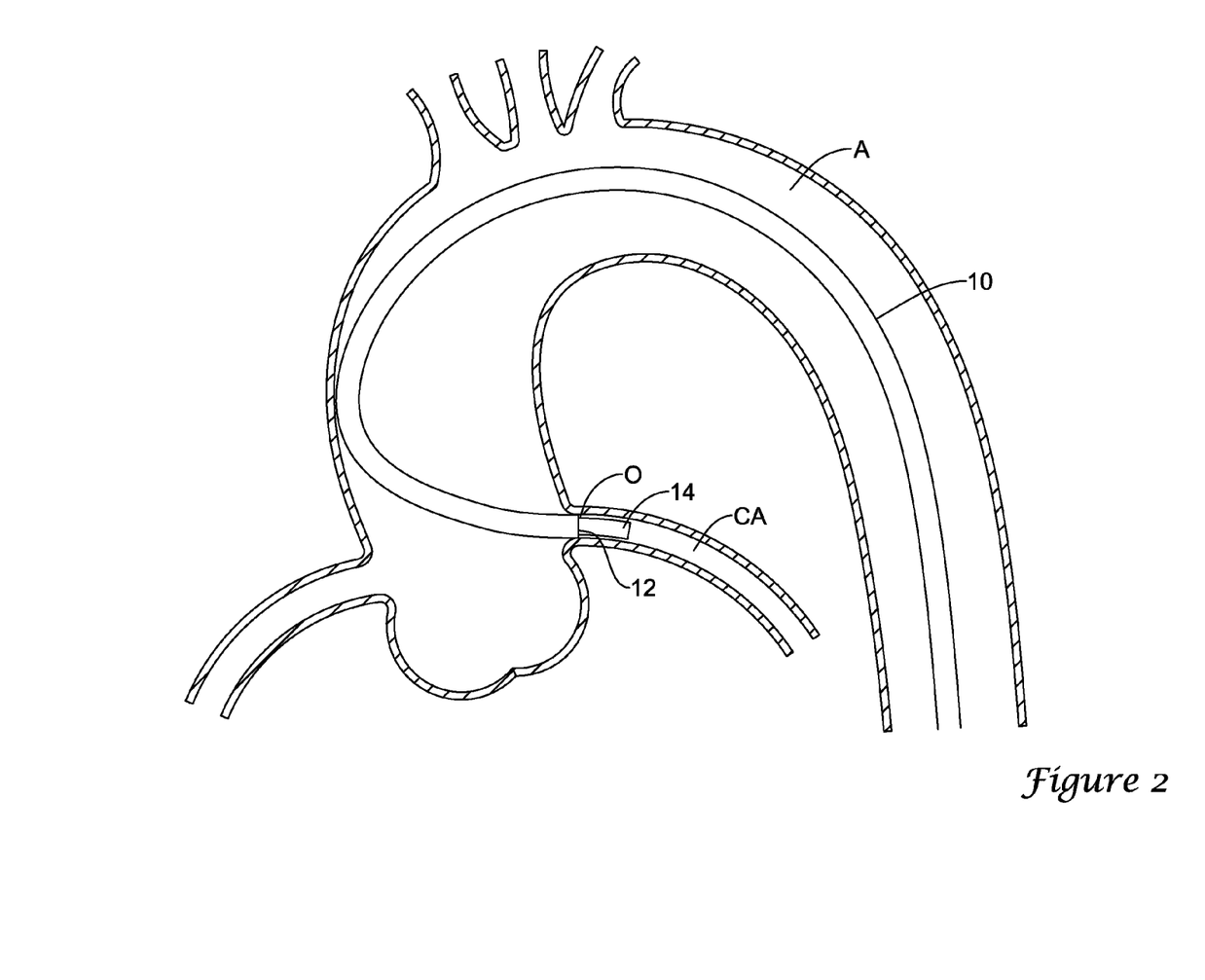
FIG. 2 is a plan view illustrating an example guide extension catheter used in conjunction with a guide catheter.

Disclosed herein are medical devices and methods for making and using medical devices that may improve access to the coronary arteries CA. For example, FIG. 2 illustrates a guide extension catheter 14 extending through guide catheter 10 and beyond distal end 12 of guide catheter 10 into the coronary artery CA. Because, for example, guide extension catheter 14 may extend beyond distal end 12 of guide catheter 10, guide extension catheter 14 may extend beyond the ostium O of the coronary artery CA and into a portion of the coronary artery CA. By extending beyond the ostium O, guide extension catheter 14 may stabilize the positioning of guide catheter 10 and allow for improved access to the coronary artery CA for a number of cardiac interventions.

Figure 3:
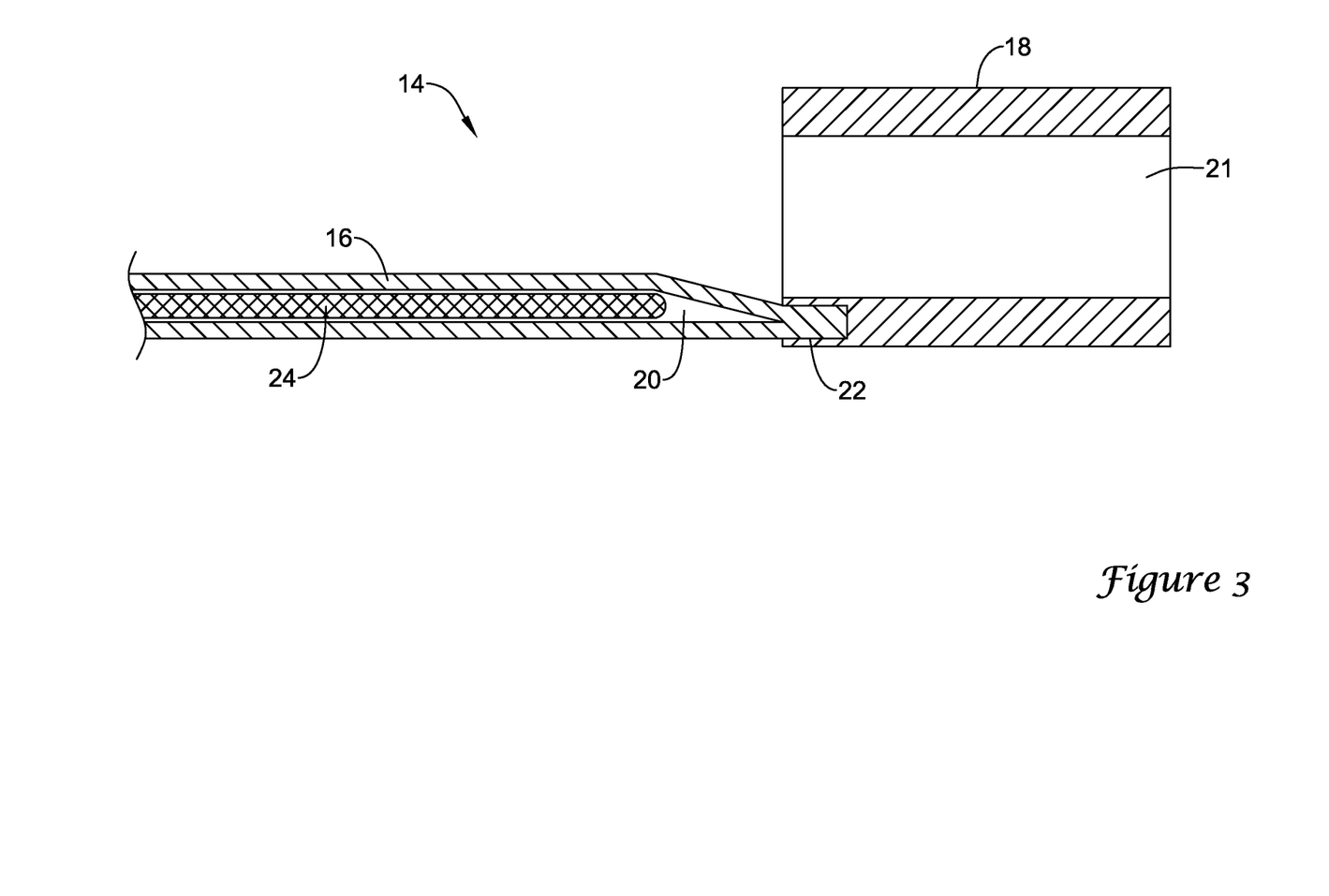
FIG. 3 is a cross-sectional side view of an example guide extension catheter.

FIG. 3 is a cross-sectional side view of guide extension catheter 14. Here it can be seen that guide extension catheter 14 may include a proximal tubular member 16 and a distal tubular member 18. Proximal tubular member 16 may define or otherwise include a lumen 20. In some embodiments, lumen 20 extends along the entire length of proximal tubular member 16. In other embodiments, lumen 20 extends along only a portion of the length of proximal tubular member 16. In addition, proximal tubular member may include both proximal and distal openings (e.g., positioned at the proximal and distal end of proximal tubular member 16) such that lumen 20 is "open" on both ends. Alternatively, one or both of the ends of proximal tubular member 16 may be closed or otherwise sealed. For example, the distal end of proximal tubular member 16 may be closed. In some of these and in other embodiments, proximal tubular member 16 may have an opening or port (not shown) formed in the wall of proximal tubular member 16 and spaced from the proximal and/or distal end of proximal tubular member 16. The port may or may not be in fluid communication with lumen 20.

Distal tubular member 18 may also define or otherwise include a lumen 21. In general, lumen 21 (and/or the inner diameter of distal tubular member 18) may be larger than lumen 20 (and/or the inner diameter of proximal tubular member 16) and may be larger than the outer diameter of proximal tubular member 16. Accordingly, lumen 21 may be sufficiently large so as to allow a therapeutic catheter (e.g., balloon catheter, stent delivery system, etc.) to pass therethrough. For example, when guide extension catheter 14 is positioned within guide catheter 10, the therapeutic catheter may extend within guide catheter 10 alongside proximal tubular member 16 and through lumen 21 of distal tubular member 18.

Distal tubular member 18 may be attached to proximal tubular member 16. The arrangement and/or configuration of the attachment between proximal tubular member 16 and distal tubular member 18 may vary. For example, distal tubular member 18 may have an opening or lumen 22 formed in tube wall thereof and proximal tubular member 16 may be disposed within opening 22. This may include necking or pinching down (in some embodiments including closing the distal end of proximal tubular member 16) proximal tubular member 16 and inserting the necked down portion into opening 22. In some embodiments, inserting proximal tubular member 16 into opening 22 may secure tubular members 16/18 via a mechanical bond. In some of these and in other embodiments, additional and/or alternative bonding may be utilized including those bonding mechanisms commonly used for medical devices (e.g., adhesive bonding, welding, thermal bonding, brazing, etc.). Other attachment mechanisms are also contemplated for attaching proximal tubular member 16 to distal tubular member 18 including direct bonding (e.g., adhesive bonding, thermal bonding, welding, brazing, etc.), bonding that is facilitated by a third component (e.g., a metal or polymer collar bonded between the proximal tubular member 16 and the distal tubular member 18), etc.

A stiffening member 24 may be slidably disposed within lumen 20. Alternatively, the stiffening member 24 may be fixed to proximal tubular member 16 within lumen 20. As the name suggests, stiffening member 24 may allow the stiffness of guide extension catheter 14 to be varied and may improve the pushability of guide extension catheter 14. For example, stiffening member 24 may be advanced distally within lumen 20 of proximal tubular member 16 (e.g., to a position at or near the distal end of proximal tubular member 16) to add enhanced stiffness to guide extension catheter 14. Likewise, stiffening member 24 can be proximally retracted or even removed completely from lumen 20 when more flexibility is desired or at another suitable time (e.g., when distal tubular member 18 is disposed within guide catheter 10 such that a portion of distal tubular member 18 extends distally beyond distal end 12 of guide catheter 10).

The materials utilized for guide extension catheter 14 (and/or the components thereof) may vary and may include any of those materials disclosed herein. In some embodiments, for example, proximal tubular member 16 may include a nickel-titanium alloy (e.g., nitinol), nylon, polyether block amide, polyurethane, and/or the like. In some embodiments, distal tubular member 18 may include a polymer. In some of these and in other embodiments, distal tubular member 18 may include a multilayer structure including, for example, an inner polymer layer, an outer polymer layer, and a reinforcement (e.g., a braid, coil, mesh, or the like) disposed therebetween. In some embodiments, stiffening member 24 may include a nickel-titanium alloy, stainless steel, etc. These are just examples. Other materials are contemplated including those disclosed herein.

A number of additional structural variations are also contemplated for guide extension catheter 14. For example, stiffening member 24 may have a variety of configurations including configurations with a stiffer proximal portion and a more flexible distal portion. In addition, the dimensions and/or configurations of stiffening member 24 may vary. In some embodiments, the outer diameter of stiffening member 24 may be smaller than the inner diameter of guide extension catheter 14 and, for example, stiffening member 24 may have a proximal outer diameter that is equal to or smaller than proximal tubular member 16.

Guide extension catheter 14 may also include a number of coatings that may, for example, reduce friction. For example, proximal tubular member 16 may have an inner and/or outer coating that includes a hydrophilic polymer that may reduce friction during tracking. An example coating may include BAYER CL-100, BIOSLIDE, NG-HPC, or the like. Stiffening member 24 may also be coated, for example, to reduce friction during tracking. For example, stiffening member 24 may be coated with silicone, SLIP COAT, MDX, or the like. These are just examples. Other materials are contemplated including those disclosed herein.

The use of guide extension catheter 14 may include advancing guide catheter 10 through a blood vessel to a position at and/or within the ostium O of a coronary artery CA, inserting a guidewire into the coronary artery CA by advancing the guidewire through guide catheter 10, and advancing guide extension catheter 14 through guide catheter 10. Stiffening member 24 may or may not be disposed within proximal tubular member 16 during advancement of guide extension catheter 14 through guide catheter 10. The position of stiffening member 24 may also be adjusted (including removal of stiffening member 24) during and/or after advancement of guide catheter extension, for example, in order to adjust the stiffness and to allow distal tubular member 18 to be positioned in the manner desired within guide catheter 10 (e.g., where a portion of distal tubular member 18 extends distally from distal end 12 of guide catheter). With guide extension catheter 14 positioned, a therapeutic catheter (e.g., balloon catheter, stent delivery system, etc.) may be advanced through guide catheter 10 and into the coronary artery CA to a position adjacent to a target region and be used perform the indicated intervention. While these example steps are provided, other methods are also contemplated where one or more of these steps is omitted or altered, as well as methods where additional steps are utilized.

Figure 4:
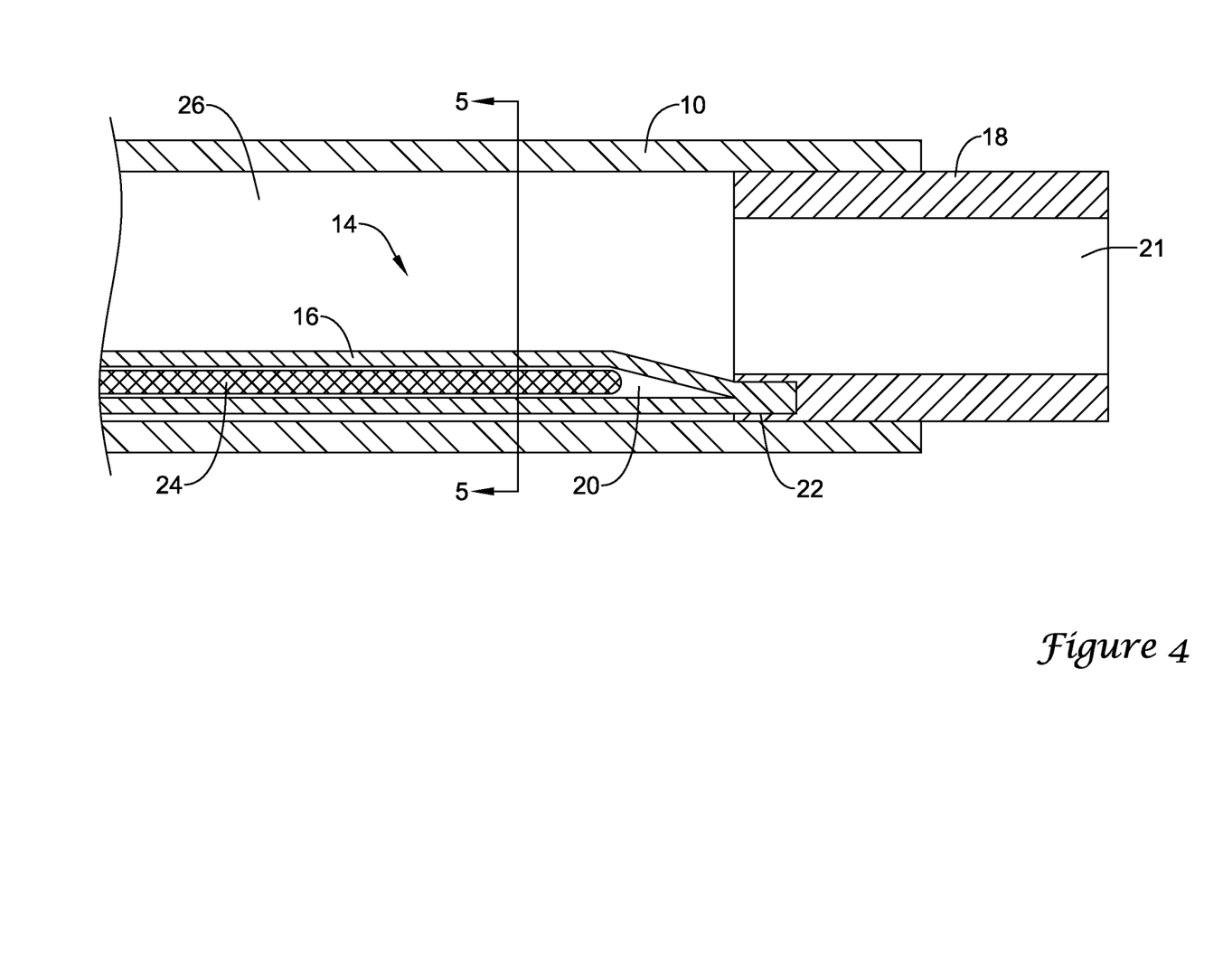
FIG. 4 is a cross-sectional side view of the example guide extension catheter and an example guide catheter.
Figure 5:
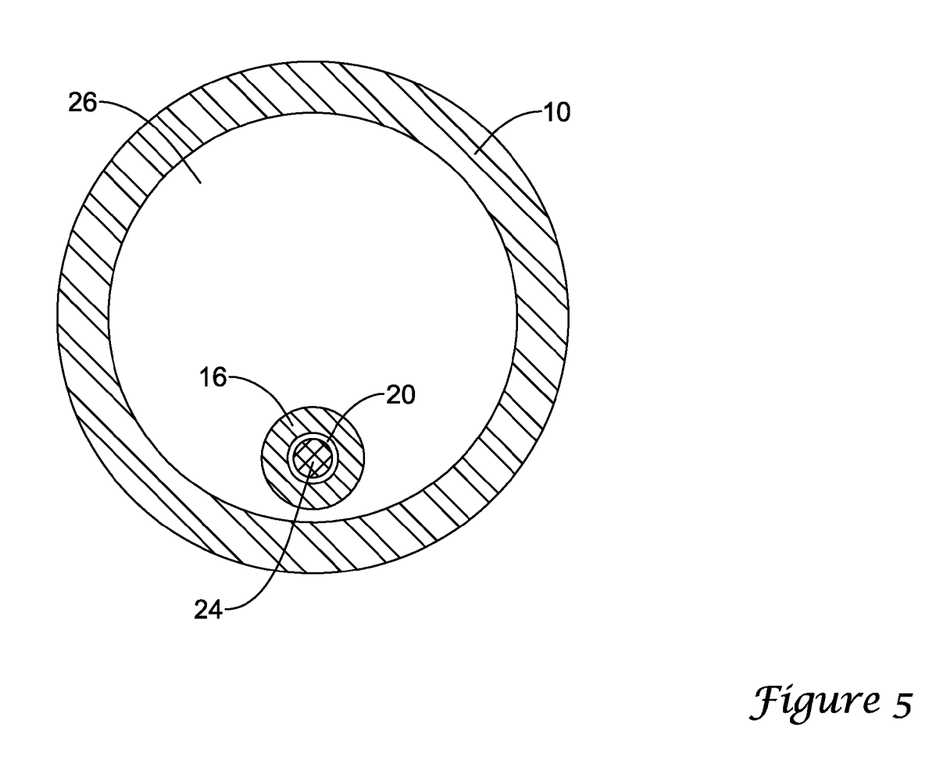
FIG. 5 is a cross-sectional view taken through line 5-5 in FIG. 4.

FIG. 4 illustrates guide extension catheter 14 disposed within guide catheter 10 (e.g., disposed within a lumen 26 defined within guide catheter 10). As shown, distal tubular member 18 may be arranged to extend distally out from distal end 12 of guide catheter 10. When so arranged, distal tubular member 18 may engage the ostium O and/or extend within a portion of the coronary artery CA to help maintain the position of guide catheter 10 and improve access to the coronary artery CA. FIG. 5 is a cross-sectional view taken through line 5-5 in FIG. 4. Here it can be seen that proximal tubular member 16 may be designed to be sufficiently small (while still being sufficiently sized and configured for pushability) so as to take up relatively little space within the interior or lumen 26 of guide catheter 10. Accordingly, the use of guide extension catheter 14 allows for a therapeutic catheter or medical device to be advanced through guide catheter 10 in order to reach the desired target location for the intervention. In some embodiments, proximal tubular member 16 may contact the inner wall surface of guide catheter 10, which may provide even more space.

Figure 6:
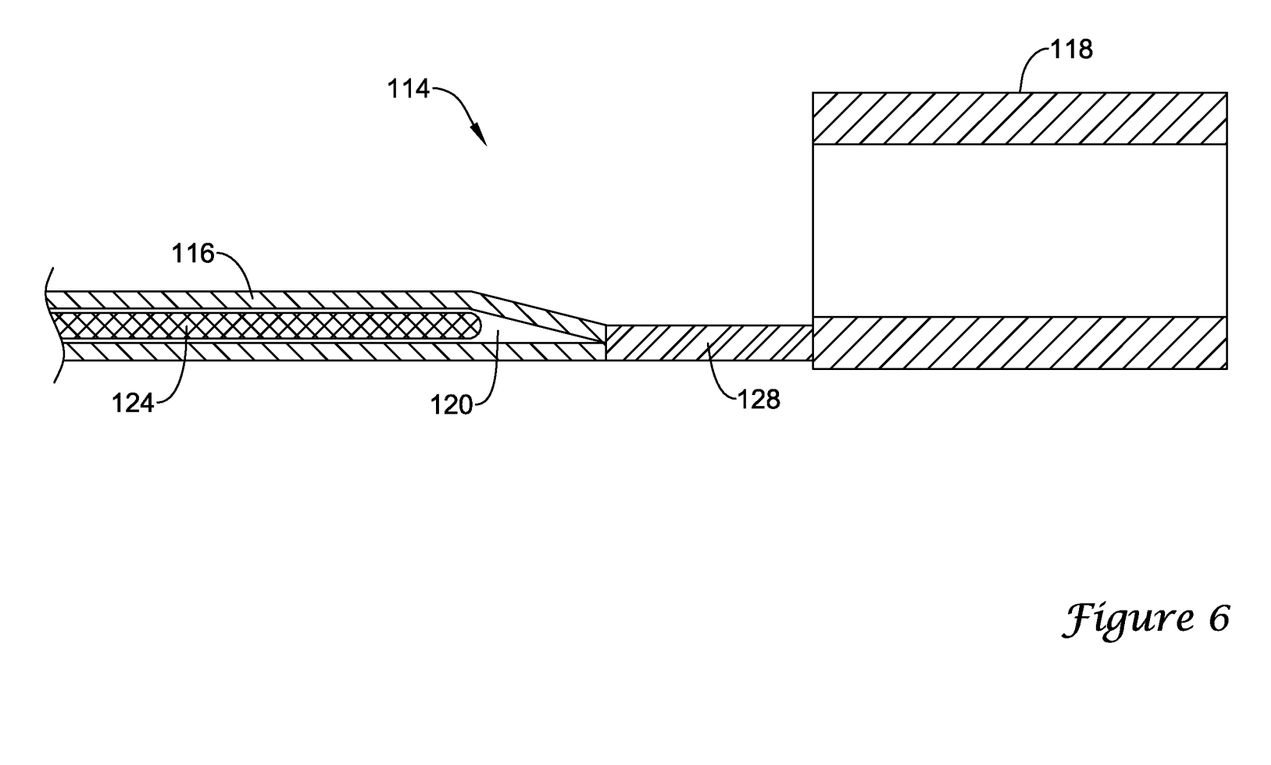
FIG. 6 is a cross-sectional side view of another example guide extension catheter.

FIG. 6 is a cross-sectional side view of another example guide extension catheter 114 that may be similar in form and function to other guide extension catheters disclosed herein. Guide extension catheter 114 may include proximal tubular member 116 and distal tubular member 118. Stiffening member 124 may be slidably disposed within lumen 120 of proximal tubular member 116. A wire member 128 may extend between and connect proximal tubular member 116 with distal tubular member 118. In some embodiments, wire member 128 may attach to a pinched off distal end of proximal tubular member 116. However, in other embodiments, wire member 128 may simply attach to proximal tubular member 116. For example, wire member 128 may be attached to an inner wall surface of proximal tubular member 116 (e.g., wire member 128 may extend within lumen 120 and attach to the inner wall surface of proximal tubular member 116), wire member 128 may be attached to an outer wall surface of proximal tubular member 116, wire member 128 may abut the distal end of proximal tubular member 116, etc.

Figure 7:
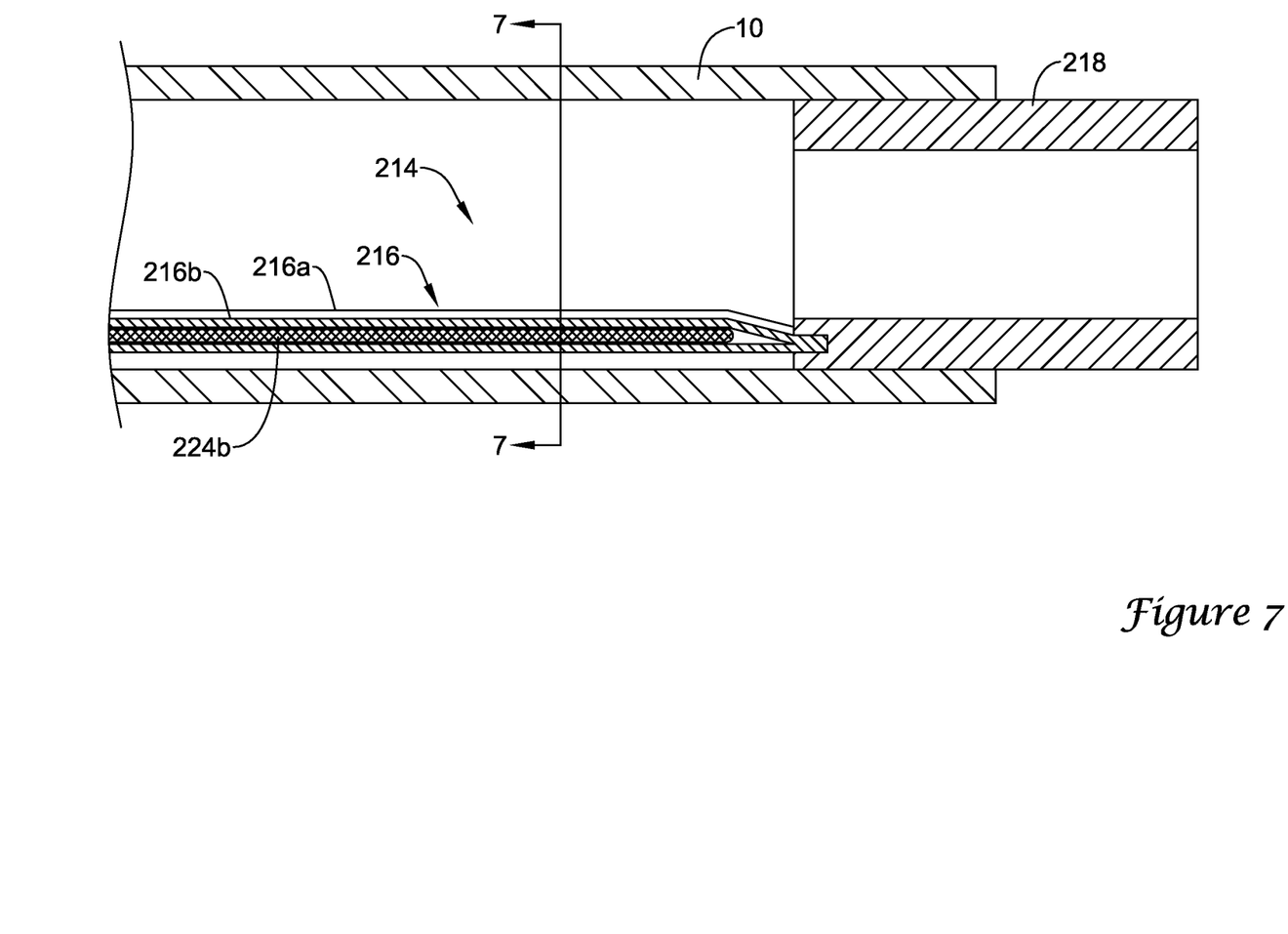
FIG. 7 is a cross-sectional side view of another example guide extension catheter and an example guide catheter.

FIG. 7 is a cross-sectional side view of another example guide extension catheter 214 that may be similar in form and function to other guide extension catheters disclosed herein. Guide extension catheter 214 may include proximal tubular member 216 and distal tubular member 218. In FIG. 7, guide extension catheter 214 is shown disposed within guide catheter 10. Proximal tubular member 216 may include a plurality of tubes, tube segments, lumens or members. For example, proximal tubular member 216 may include three tubular members 216a/216b/216c (which can be seen in FIG. 8) that collectively define proximal tubular member 216. Tubular members 216a/216b/216c may be attached to one another (e.g., with an adhesive bond, thermal bond, weld, braze, etc.) or a sleeve (not shown) may be disposed about tubular members 216a/216b/216c to attach tubular members 216a/216b/216c to one another. In other embodiments, tubular members 216a/216b/216c may not be attached to one another. One or more stiffening members 224a/224b/224c may be disposed within tubular members 216a/216b/216c, which may have a similar form and function to other stiffening members disclosed herein.

Figure 8:
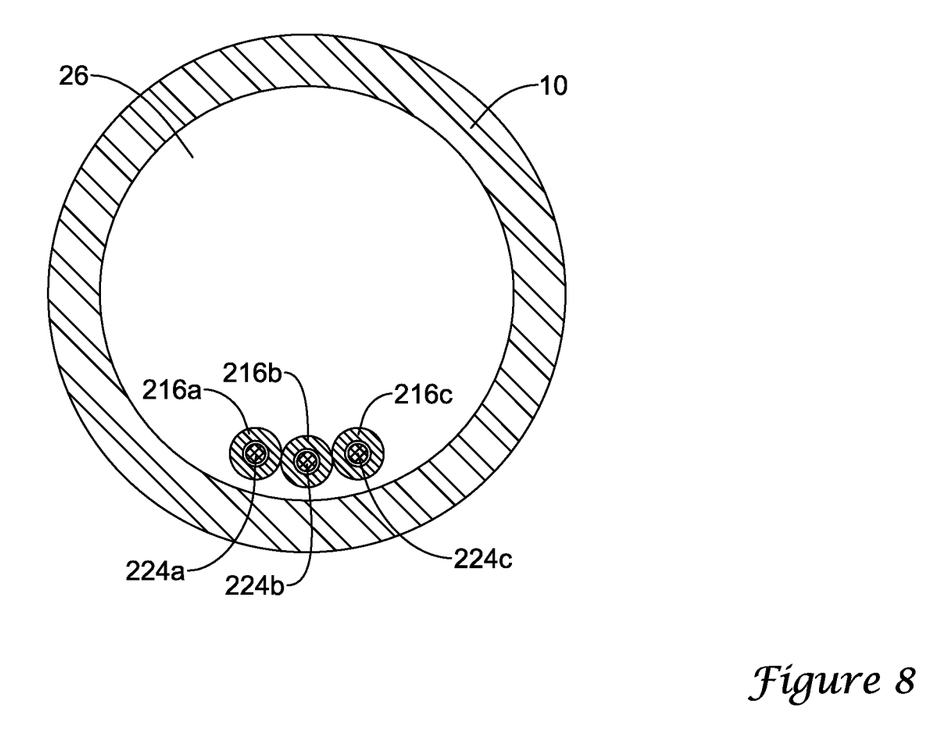
FIG. 8 is a cross-sectional view taken through line 8-8 in FIG. 7.

While proximal tubular member 216 is illustrated as including three tubular members 216a/216b/216c, this is not intended to be limiting as any suitable number of tubular members may be utilized (e.g., one, two, three, four, five, six, seven, eight, nine, ten, etc.).

FIG. 8 is a cross-sectional view taken through line 8-8 in FIG. 7. Here, an example arrangement of tubular members 216a/216b/216c can be seen. For example, tubular members 216a/216b/216c may be arranged in an arcuate or curved arrangement that may follow or trace the interior wall of guide catheter 10. This may improve the amount of space within guide catheter 10 through which a treatment catheter may be advanced through. In some embodiments, tubular members 216a/216b/216c may contact the inner wall surface of guide catheter 10, which may provide even more space.

Figure 9:
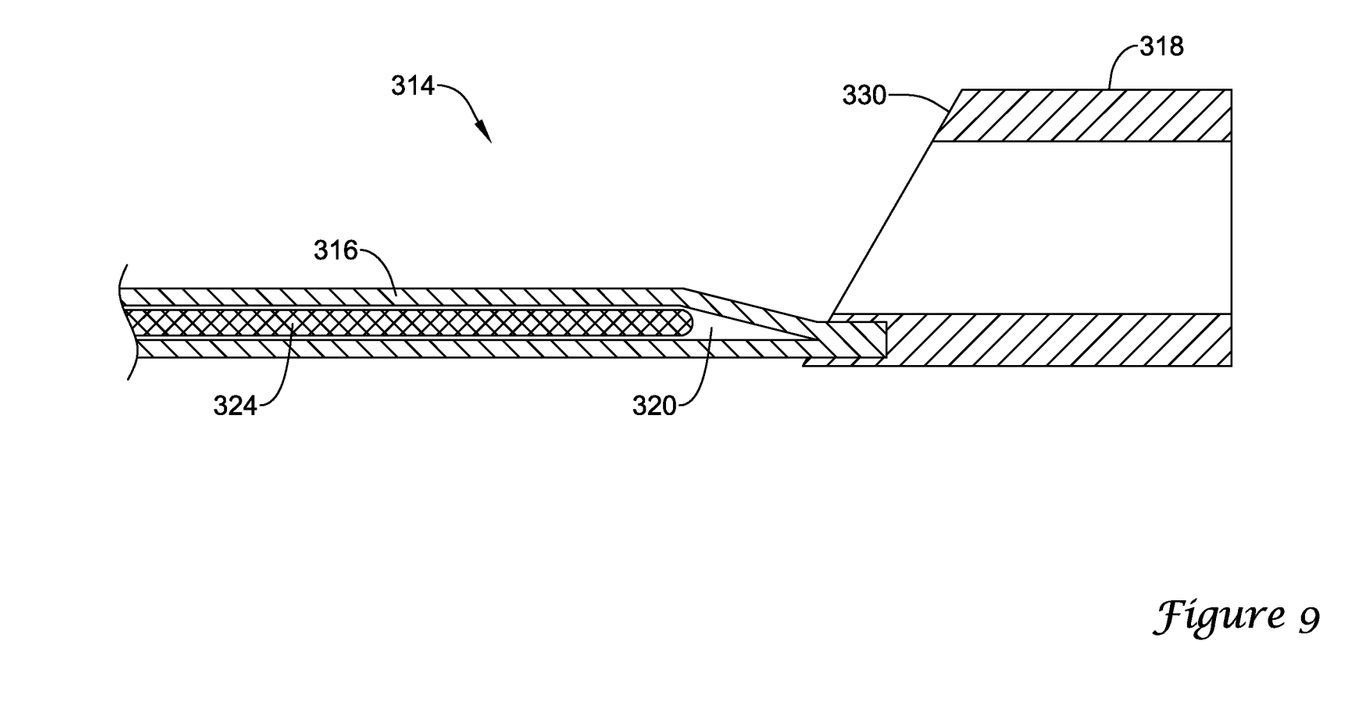
FIG. 9 is a cross-sectional side view of another example guide extension catheter.

FIG. 9 is a cross-sectional side view of another example guide extension catheter 314 that may be similar in form and function to other guide extension catheters disclosed herein. Guide extension catheter 314 may include proximal tubular member 316 and distal tubular member 318. Stiffening member 324 may be slidably disposed within lumen 320 of proximal tubular member 316. In this example, distal tubular member 318 may include a skived or slanted proximal end 330.

Figure 10:
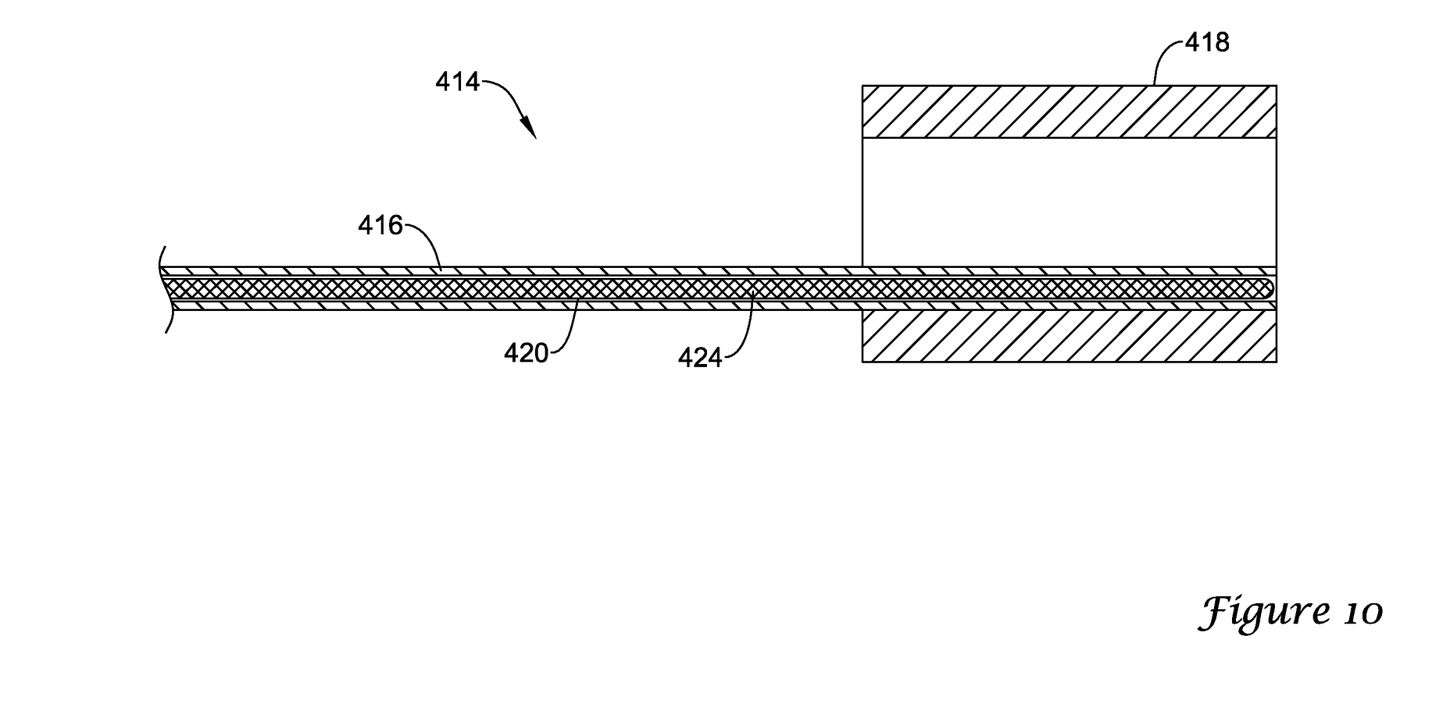
FIG. 10 is a cross-sectional side view of another example guide extension catheter.

FIG. 10 is a cross-sectional side view of another example guide extension catheter 414 that may be similar in form and function to other guide extension catheters disclosed herein. Guide extension catheter 414 may include proximal tubular member 416 and distal tubular member 418. In this example, proximal tubular member 416 may extend within distal tubular member 418. For example, proximal tubular member 416 may extend along an interior wall surface of distal tubular member 418 to a position at or near the distal end of distal tubular member 418. In some embodiments, the outer wall surface of proximal tubular member 416 may be attached to the inner wall surface of distal tubular member 418.

In some embodiments, proximal tubular member 416 may have an open distal end. However, in other embodiments, proximal tubular member 416 may be necked down and/or sealed at its distal end. This may prevent fluid from travelling flowing through lumen 420 and out from the patient during an intervention.

Stiffening member 424 may extend through lumen 420 of proximal tubular member 416. Because proximal tubular member 416 may be disposed within distal tubular member 418, stiffening member 424 may also extend within distal tubular member 418 (e.g., while within proximal tubular member 416). In some embodiments, proximal tubular member 416 may terminate proximally of the distal end of distal tubular member 418. In these embodiments, stiffening member 424 may extend distally from proximal tubular member 416 and within distal tubular member 418.

The materials that can be used for the various components of the guide extension catheters disclosed herein may vary. For simplicity purposes, the following discussion makes reference to proximal tubular member 16 and distal tubular member 18. However, this is not intended to limit the devices and methods described herein, as the discussion may be applied to other similar tubular members and/or components of tubular members or devices disclosed herein.

Proximal tubular member 16 and distal tubular member 18 and/or other components of guide extension catheter 14 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of proximal tubular member 16 and/or distal tubular member 18 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guide extension catheter 14 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guide extension catheter 14 to achieve the same result.

In some embodiments, a degree of Magnetic Resonance Imaging (MRI) compatibility is imparted into guide extension catheter 14. For example, proximal tubular member 16 and distal tubular member 18, or portions thereof, may be made of a material that does not substantially distort the image and create substantial artifacts (i.e., gaps in the image). Certain ferromagnetic materials, for example, may not be suitable because they may create artifacts in an MRI image. Proximal tubular member 16 and distal tubular member 18, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of proximal tubular member 16 and distal tubular member 18 that may define a generally smooth outer surface for guide extension catheter 14. In other embodiments, however, such a sheath or covering may be absent from a portion of all of guide extension catheter 14, such that proximal tubular member 16 and distal tubular member 18 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guide extension catheter 14 (including, for example, the exterior surface of proximal tubular member 16 and distal tubular member 18) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of proximal tubular member 16 and distal tubular member 18, or other portions of guide extension catheter 14. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A guide extension catheter, comprising:
   a proximal tubular member having a proximal end, a distal end, and a lumen defined therein and extending between the proximal end and the distal end of the proximal tubular member, the proximal end is an open proximal end and the distal end is a closed distal end;

a distal tubular member having a proximal end region attached to the distal end of the proximal tubular member, the distal tubular member having a lumen with a proximal terminal opening adjacent the proximal end region of the distal tubular member and the distal end of the proximal tubular member, and a distal terminal opening adjacent a distal end region of the distal tubular member and spaced distally from the distal end of the proximal tubular member;

wherein the proximal tubular member has an outer diameter, wherein the lumen of the distal tubular member has a constant inner diameter, and wherein the inner diameter of the lumen of the distal tubular member is greater than the outer diameter of the proximal tubular member; and a stiffening member slidably and removably disposed within the proximal tubular member for varying a stiffness of the guide extension catheter by advancing or retracting the stiffening member in the proximal tubular member.

2. The guide extension catheter of claim 1, wherein the proximal tubular member includes nickel-titanium alloy.

3. The guide extension catheter of claim 1, wherein the distal tubular member includes an inner polymer layer, an outer polymer layer, and a reinforcement layer disposed between the inner polymer layer and the outer polymer layer.

4. The guide extension catheter of claim 1, wherein the stiffening member includes stainless steel.

5. The guide extension catheter of claim 1, wherein the distal tubular member has a wall lumen formed in a tube wall of the distal tubular member and wherein the proximal tubular member is disposed in the wall lumen.

6. The guide extension catheter of claim 1, wherein the proximal tubular member is attached to the distal tubular member with a wire member that extends between the distal end of the proximal tubular member and the proximal end region of the distal tubular member.

7. The guide extension catheter of claim 1, wherein:
the proximal tubular member includes a plurality of tubes that are coupled to one another; and
each of the plurality of tubes are coupled to one another by being attached to at least one other of the plurality of tubes.

8. The guide extension catheter of claim 1, wherein the proximal end region of the distal tubular member is skived.

9. The guide extension catheter of claim 1, wherein the guide extension catheter is disposed within a guide catheter.

10. The guide extension catheter of claim 9, wherein the distal tubular member has an outer diameter that is substantially the same as the inner diameter of the guide catheter.

11. The guide extension catheter of claim 9, wherein a treatment catheter is disposed within the guide catheter.

12. The guide extension catheter of claim 1, wherein the lumen of the distal tubular member is the only lumen of the distal tubular member.

13. The guide extension catheter of claim 1, wherein the lumen of the proximal tubular member is the only lumen of the proximal tubular member.

14. A catheter system for improving access to a coronary artery, the catheter system comprising:
a guide catheter having a distal end;
a guide extension catheter disposed within the guide catheter, the guide extension catheter including:
a proximal tubular member having a proximal end, a distal end, and a lumen defined therein and extending between the proximal end and the distal end of the proximal tubular member, a distal tubular member having a proximal end region attached to the distal end of the proximal tubular member with a wire that extends between the distal end of the proximal tubular member and the proximal end region of the distal tubular member, wherein the distal tubular member has a lumen having a constant inner diameter, the lumen having a proximal terminal opening adjacent the proximal end region of the distal tubular member and a distal terminal opening adjacent a distal end region of the distal tubular member, the distal terminal opening is spaced distally from the distal end of the proximal tubular member, and a stiffening member slidably and removably disposed within the proximal tubular member for varying a stiffness of the guide extension catheter by advancing or retracting the stiffening member in the proximal tubular member;

wherein a distal end of the guide extension catheter is configured to extend distally beyond the distal end of the guide catheter and into a coronary artery; and a treatment catheter disposed within the guide catheter.

15. The catheter system of claim 14, wherein:
the proximal tubular member includes a plurality of tubes that are coupled to one another; and
each of the plurality of tubes are coupled to one another by being attached to at least one other of the plurality of tubes.

16. The catheter system of claim 14, wherein the proximal end region of the distal tubular member is skived.

17. A method for accessing a coronary artery, the method comprising:
providing a guide catheter;
advancing the guide catheter through a blood vessel to a position adjacent to an ostium of a coronary artery;
providing a guide extension catheter, the guide extension catheter comprising:
a proximal tubular member having a proximal end, a distal end, and a lumen defined therein and extending between the proximal end and the distal end of the proximal tubular member, the proximal end is an open proximal end and the distal end is a closed distal end, a distal tubular member having a proximal end region attached to the distal end of the proximal tubular member, the distal tubular member having a lumen with a proximal opening adjacent the proximal end region of the distal tubular member and a distal opening adjacent a distal end region of the distal tubular member and spaced distally from the distal end of the proximal tubular member, wherein the proximal tubular member has an outer diameter, wherein the lumen of the distal tubular member has a constant inner diameter, and wherein the inner diameter of the lumen of the distal tubular member is greater than the outer diameter of the proximal tubular member, and a stiffening member slidably and removably disposed within the proximal tubular member for varying a stiffness of the guide extension catheter by advancing or retracting the stiffening member in the proximal tubular member;

advancing the guide extension catheter through the guide catheter to a location where at least a portion of the distal tubular member extends distally beyond a distal end of the guide catheter and into the coronary artery; and advancing a treatment catheter through the guide catheter.

* * * * *